(12) United States Patent
Gunawan et al.

(10) Patent No.: US 10,031,058 B2
(45) Date of Patent: Jul. 24, 2018

(54) PARALLEL DIPOLE LINE TRAP VISCOMETER AND PRESSURE GAUGE

(71) Applicant: International Business Machines Corporation, Armonk, NY (US)

(72) Inventors: Oki Gunawan, Fair Lawn, NJ (US); Yudistira Virgus, Williamsburg, VA (US)

(73) Assignee: International Business Machines Corporation, Armonk, NY (US)

( * ) Notice: Subject to any disclaimer, the term of this patent is extended or adjusted under 35 U.S.C. 154(b) by 166 days.

(21) Appl. No.: 14/826,934

(22) Filed: Aug. 14, 2015

(65) Prior Publication Data
US 2017/0045433 A1 Feb. 16, 2017

(51) Int. Cl.
*G01N 11/16* (2006.01)
*G01N 27/00* (2006.01)
*G01N 11/14* (2006.01)

(52) U.S. Cl.
CPC ............ *G01N 11/16* (2013.01); *G01N 27/00* (2013.01); *G01N 2011/147* (2013.01)

(58) Field of Classification Search
CPC ........ G01N 11/00; G01N 11/02; G01N 11/08; G01N 11/14; G01N 11/10; G01N 11/16; G01N 9/002; G01N 11/162; G01N 24/081; G01N 2291/02818; G01L 9/00; G01L 23/00
USPC ............ 73/54.01, 54.23, 54.24, 54.25, 31.04
See application file for complete search history.

(56) References Cited

U.S. PATENT DOCUMENTS

| | | | |
|---|---|---|---|
| 5,191,316 A | 3/1993 | Dreyer | |
| 6,477,901 B1 | 11/2002 | Tadigadapa et al. | |
| 6,711,942 B2 | 3/2004 | Getman et al. | |
| 7,024,319 B2 | 4/2006 | Mueller et al. | |
| 7,647,813 B2 | 1/2010 | Pavlovsky | |
| 8,689,614 B2 | 4/2014 | Day et al. | |
| 8,756,980 B2 | 6/2014 | D'Angelico et al. | |
| 8,895,355 B2 | 11/2014 | Cao et al. | |
| 2003/0090593 A1* | 5/2003 | Xiong | H04N 5/23248 348/620 |

(Continued)

OTHER PUBLICATIONS

G.P. Matthews et al., "An effective isotropic pair potential energy function for carbon dioxide," Chemical Physics Letters, vol. 155, issue 6, pp. 518-520 (Mar. 1989).
T.C. Davenport, "Viscosity in the petroleum industry," Physics Education 3, 139 (May 1968).
J. Wilhelm, et al., "An improved Greenspan acoustic viscometer," International Journal of Thermophysics, vol. 21, issue 5, pp. 983-997 (Sep. 2000).

(Continued)

*Primary Examiner* — John Fitzgerald
*Assistant Examiner* — Truong D Phan
(74) *Attorney, Agent, or Firm* — Vazken Alexanian; Michael J. Chang, LLC

(57) ABSTRACT

Techniques for gas analysis using a parallel dipole line (PDL) trap viscometer are provided. In one aspect, a gas analysis system is provided which includes: a PDL trap including: a pair of diametric cylindrical magnets, and a diamagnetic rod levitating above the magnets; and a motion detector for capturing motion of the diamagnetic rod. The motion detector can include a digital video camera positioned facing a top of the PDL trap so as to permit capturing video images of the diamagnetic rod and the system can include a computer for receiving and analyzing video images from the video camera. Methods for measuring gas viscosity and pressure using the PDL trap system are also provided.

19 Claims, 4 Drawing Sheets

(56) References Cited

U.S. PATENT DOCUMENTS

| | | | |
|---|---|---|---|
| 2004/0227817 A1* | 11/2004 | Oya | G06F 3/017 348/155 |
| 2007/0289376 A1* | 12/2007 | Wagner | G01N 9/002 73/32 A |
| 2009/0033745 A1* | 2/2009 | Yeredor | G01S 3/7864 348/152 |
| 2010/0140213 A1* | 6/2010 | Mizukami | B03C 1/08 216/22 |
| 2011/0167909 A1* | 7/2011 | Wagner | G01N 9/002 73/32 A |
| 2011/0226064 A1* | 9/2011 | Dreyer | G01F 23/2967 73/632 |
| 2014/0273449 A1* | 9/2014 | Cao | H01L 21/02697 438/674 |
| 2015/0009331 A1* | 1/2015 | Venkatraman | B61L 23/042 348/148 |
| 2016/0232410 A1* | 8/2016 | Kelly | G06K 9/00711 |
| 2017/0035330 A1* | 2/2017 | Bunn | A61B 5/1128 |

OTHER PUBLICATIONS

K.A. Gillis, et al., "Theory of the Greenspan viscometer," The Journal of the Acoustical Society of America 114, pp. 166-173 (Jul. 2003).

K.A. Gillis et al., "Greenspan acoustic viscometer for gases," Rev. Sci. Instr. 67, 1850 (Jun. 1996).

Gunawan et al., "A parallel dipole line system," Applied Physics Letters 106, 062407 (Feb. 2015).

Fluid Dynamic Drag, Hoerner, Hoerner Fluid Dynamics, Chapter 3, p. 12 (3-12), 1965.

Boffito et al., "Spinning rotor gauge in the range from 10-4 Pa to atmosphere," J. Vac. Sci. Technol. A 15(4), pp. 2391-2394, Jul./Aug. 1997.

D. Badiane et al., "Vibrating beam in viscous fluid for viscosity sensing: application to an industrial vibrating viscometer," Proceedings of the 12th Pan-American Congress of Applied Mechanics, 2012, 6 pages.

* cited by examiner

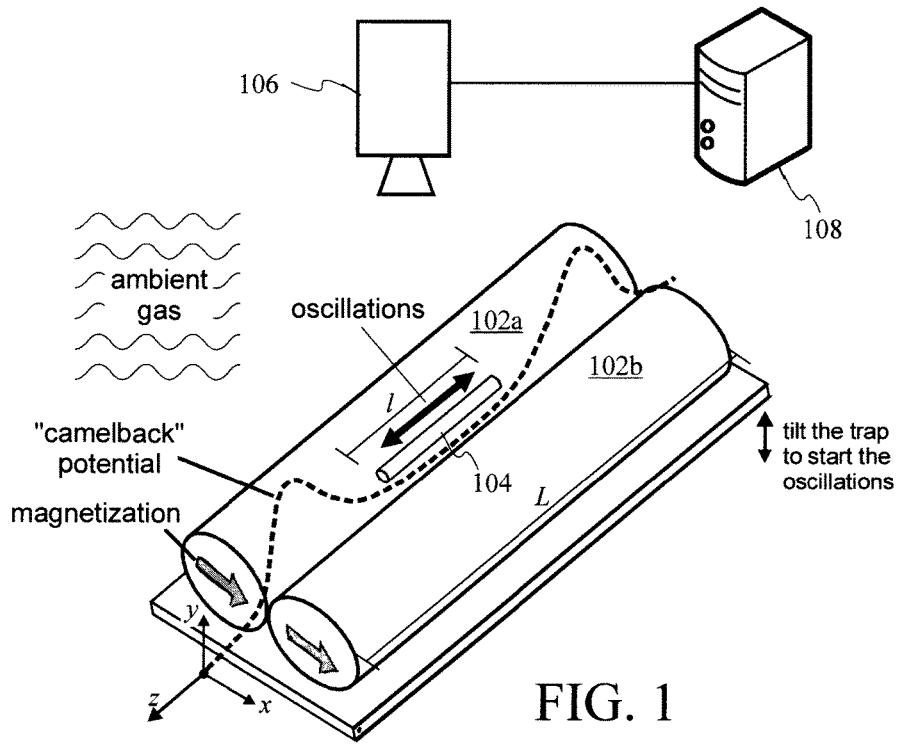
FIG. 1
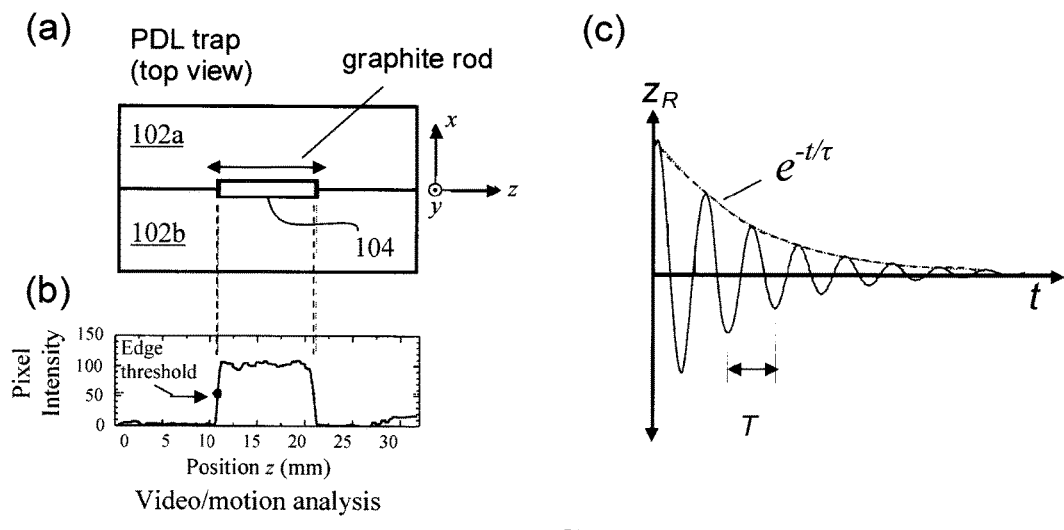
FIGS. 2a-c

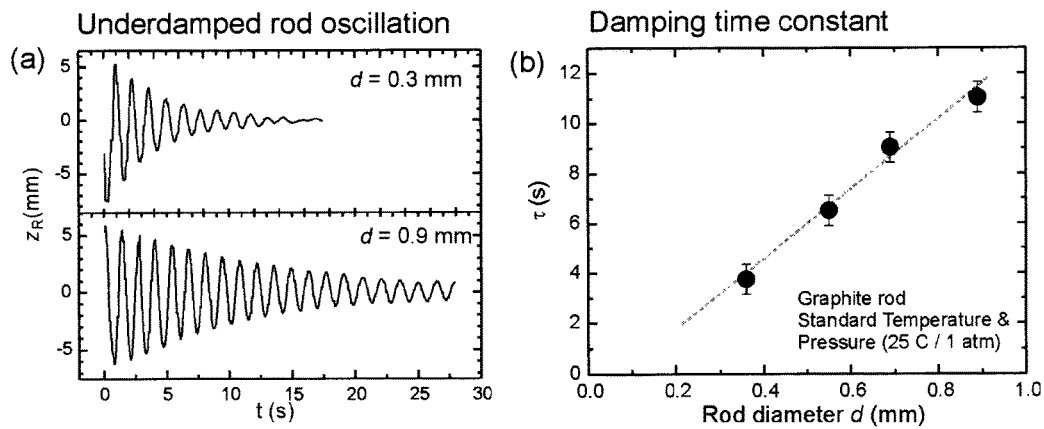
FIGS. 3a-b
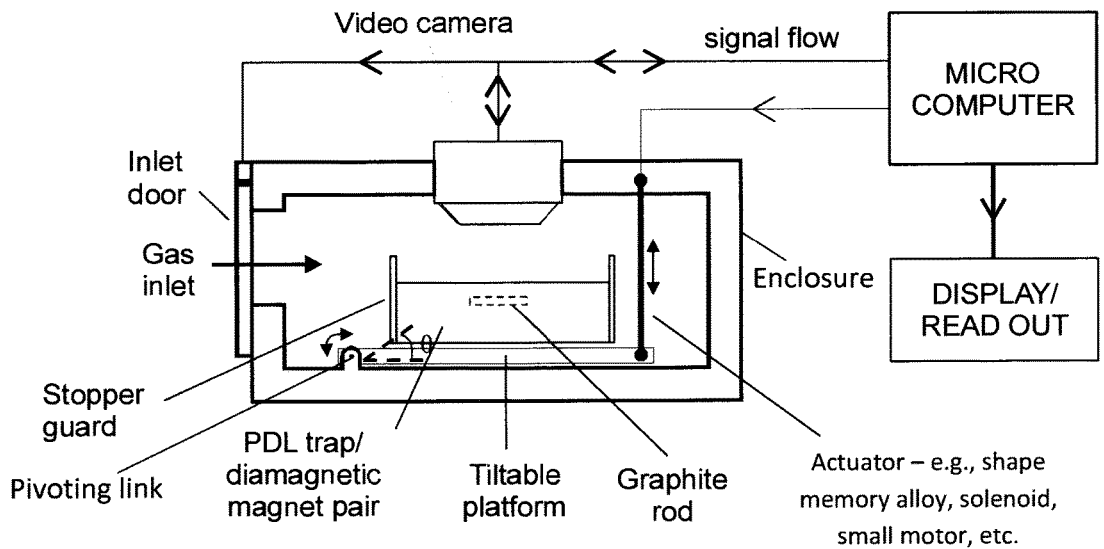
FIG. 4

PARALLEL DIPOLE LINE TRAP VISCOMETER AND PRESSURE GAUGE

FIELD OF THE INVENTION

The present invention relates to techniques for gas viscosity and pressure analysis, and more particularly, to gas viscosity and pressure analysis using a parallel dipole line (PDL) trap viscometer.

BACKGROUND OF THE INVENTION

Viscosity and pressure are two important physical parameters of a gas that often need to be measured. Viscosity is a measure of fluid (or gas) resistance to gradual deformation by shear or tensile stress. It provides information about thermal-physical property and can also be used to probe intermolecular potentials. See, for example, G. P. Matthews et al., "An effective isotropic pair potential energy function for carbon dioxide," Chemical Physics Letters, vol. 155, issue 6, pgs. 518-520 (March 1989). In industrial setting, viscosity measurement is also of great importance. For example, the viscosity of hydrocarbon gases is an important factor in the petroleum industry. See, for example, T. C. Davenport, "Viscosity in the petroleum industry," Physics Education 3, 139 (May 1968). It affects the quantity that can be recovered from a reservoir. In the semiconductor industry, the viscosity data of highly reactive gases used in semiconductor processing are needed to calibrate mass-flow controllers and to model processes such as chemical vapor deposition. See, for example, J. Wilhelm, et al., "An improved Greenspan acoustic viscometer," International Journal of Thermophysics, vol. 21, issue 5, pgs. 983-997 (September 2000); and K. A. Gillis, et al., "Theory of the Greenspan viscometer," The Journal of the Acoustical Society of America 114, pgs. 166-173 (July 2003).

The most common viscometers are falling ball viscometers, capillary tube viscometers, oscillating-piston viscometers, vibrational viscometers, and rotational viscometers—most of which measure liquid viscosity. The measurement of gas viscosity is more challenging since the density and the viscosity of gases are much lower. Thus modification of these viscometers is needed in order to measure the viscosity of a gas.

One well-known viscometer for measuring gas viscosity is a double Helmholtz acoustic resonator. See, for example, K. A. Gillis et al., "Greenspan acoustic viscometer for gases," Rev. Sci. Instr. 67, 1850 (June 1996). The performance of this viscometer device, however, depends on the response function of the system (which is determined by the geometry of the system and the gas properties) and the instrumentation setup is rather complex. As a result, this device cannot be used to measure the viscosity of a wide range of gases.

Gas or vacuum pressure measurement is also routinely needed. Various pressure gauges are already available however they need to be calibrated with other gauge and has limited accuracy. Very accurate vacuum pressure gauge based on gas viscosity measurement can be obtained using a spinning rotor gauge. However, this instrument is complex and expensive.

Therefore, an improved and more cost effective gas analysis apparatus that can be used to measure viscosity and pressure in a wide range of gases would be desirable.

SUMMARY OF THE INVENTION

The present invention provides techniques for gas analysis using a parallel dipole line (PDL) trap viscometer. In one aspect of the invention, a gas analysis system is provided. The gas analysis system includes: a PDL trap including: a pair of diametric cylindrical magnets, and a diamagnetic rod levitating above the pair of diametric cylindrical magnets; and a motion detector for capturing motion of the diamagnetic rod. The motion detector can include a digital video camera positioned facing a top of the PDL trap so as to permit capturing video images of the diamagnetic rod and the system can include a computer for receiving and analyzing video images from the video camera.

In another aspect of the invention, a method for analyzing a gas is provided. The method includes the steps of: providing a gas analysis system having i) a PDL trap having a pair of diametric cylindrical magnets, and a diamagnetic rod levitating above the pair of diametric cylindrical magnets; and ii) a motion detector for capturing motion of the diamagnetic rod, wherein the PDL trap is encased within an enclosure; introducing the gas to the enclosure; initiating oscillation of the diamagnetic rod over the pair of diametric cylindrical magnets; recording motion of the diamagnetic rod using the motion detector; determining a damping time constant $\tau$ from the recorded motion of the diamagnetic rod; and calculating a viscosity $\mu$ of the gas using the damping time constant $\tau$ wherein, for example, $\mu = k_V/\tau$, and wherein $k_V$ is a viscosity measurement calibration factor for the gas analysis system and is independent of the gas being analyzed.

In yet another aspect of the invention, another method for analyzing a gas is provided. The method includes the steps of: providing a gas analysis system having i) a PDL trap having a pair of diametric cylindrical magnets, and a diamagnetic rod levitating above the pair of diametric cylindrical magnets; and ii) a motion detector for capturing motion of the diamagnetic rod, wherein the PDL trap is encased within an enclosure; introducing the gas to the enclosure; initiating oscillation of the diamagnetic rod over the pair of diametric cylindrical magnets; recording motion of the diamagnetic rod using the motion detector; determining a damping time constant $\tau$ from the recorded motion of the diamagnetic rod; and calculating a pressure p of the gas using the damping time constant $\tau$ wherein, for example, $\mu = k_P/\tau$, and wherein $k_P$ is a pressure measurement calibration factor for the gas analysis system and is independent of the gas being analyzed.

A more complete understanding of the present invention, as well as further features and advantages of the present invention, will be obtained by reference to the following detailed description and drawings.

BRIEF DESCRIPTION OF THE DRAWINGS

FIG. 1 is a diagram illustrating a parallel dipole line (PDL) trap viscometer system according to an embodiment of the present invention;

FIG. 2a is a diagram illustrating a top-down view of the PDL trap viscometer system according to an embodiment of the present invention;

FIG. 2b is a diagram illustrating video motion analysis being used to extract the motion of a diamagnetic rod of the PDL trap viscometer system according to an embodiment of the present invention;

FIG. 2c is a diagram illustrating underdamped oscillation of the diamagnetic rod according to an embodiment of the present invention;

FIG. 3a is a diagram illustrating underdamped oscillation with rods of different diameters according to an embodiment of the present invention;

FIG. 3b is a diagram illustrating damping time constant versus rod diameter according to an embodiment of the present invention;

FIG. 4 is a diagram of one exemplary configuration of the present PDL trap system according to an embodiment of the present invention;

DETAILED DESCRIPTION OF PREFERRED EMBODIMENTS

Figure 5:
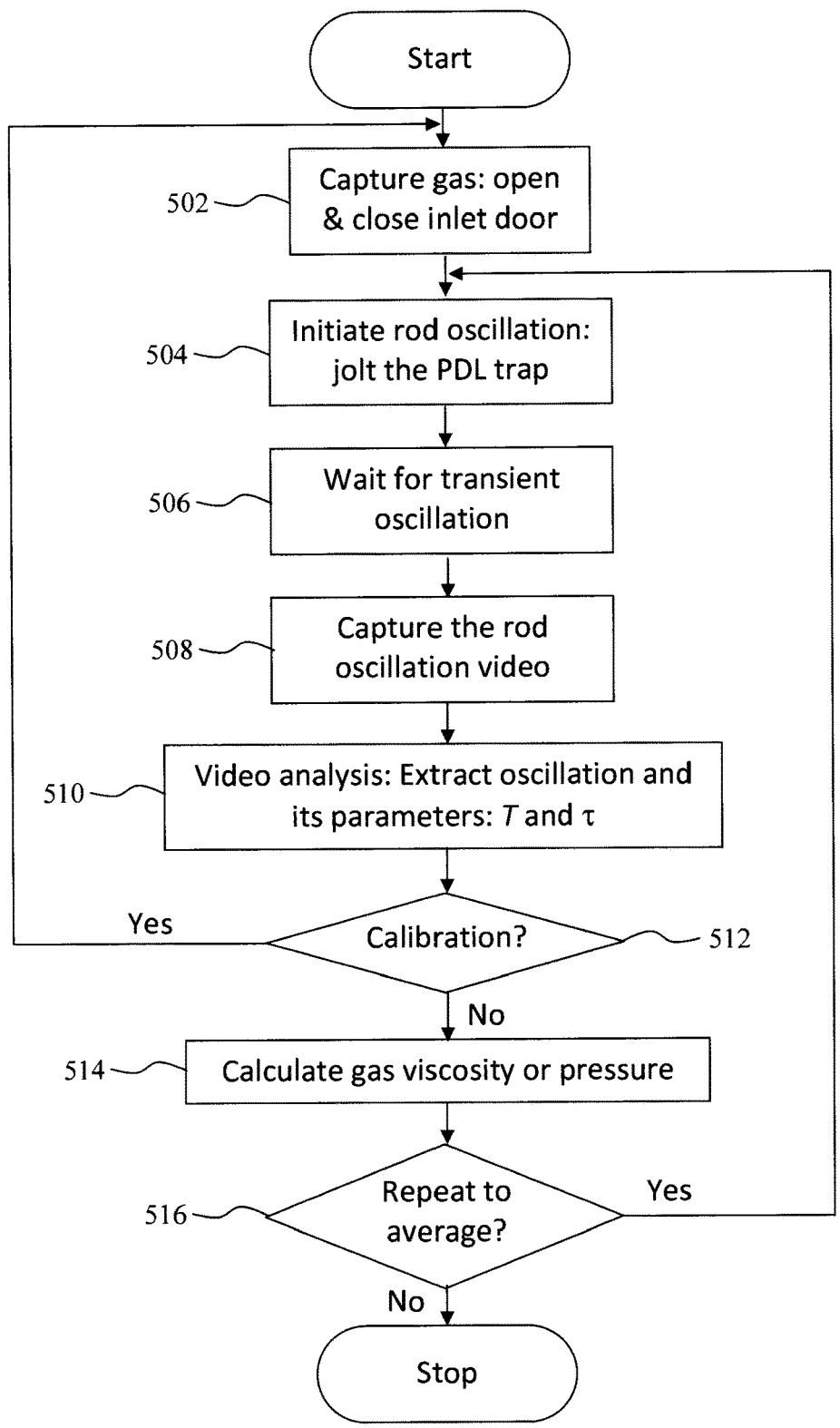
FIG. 5 is a diagram of an exemplary methodology for analyzing a gas using the present PDL trap system according to an embodiment of the present invention.

Provided herein are techniques for measuring the viscosity of an ambient gas utilizing an oscillating graphite rod trapped in a parallel dipole line system. By capturing the oscillation (e.g., using video), the damping lifetime of the oscillation can be extracted and the viscosity of the gas can be calculated. The system can also be utilized to measure pressure in a vacuum chamber at low pressure p regime (e.g., p<$10^{-4}$ bar). Compared to other existing technology, this system is compact, low cost, can be miniaturized, and can be used to measure wide range of gases The present system makes use of an oscillating graphite rod trapped in a parallel dipole line (PDL) trap system. For a general description of a PDL trap system see, for example, Gunawan et al., "A parallel dipole line system," Applied Physics Letters 106, 062407 (February 2015) (hereinafter "Gunawan"); and U.S. Pat. No. 8,895,355 issued to Cao et al., entitled "Magnetic Trap for Cylindrical Diamagnetic Materials," the contents of each of which are incorporated by reference as if fully set forth herein.

A general overview of the present PDL trap-based gas analysis system and use thereof to measure viscosity and/or pressure of an ambient gas is provided in FIG. 1. As shown in FIG. 1, the present PDL trap gas analysis system includes a pair of diametric cylindrical magnets 102a and 102b in which a diamagnetic rod 104, such as a graphite rod, is trapped. The diametric magnet has magnetization along the diameter of the magnet as shown in FIG. 1. Namely, as described in Gunawan a cylindrical rod immersed in the magnetic field of the diametric magnets will have an induced magnetization. Since the rod is diamagnetic, the induced magnetization is opposite to the magnetic field and tends to move it towards a region with minimum field and produces levitation of trapping effect. Thus, the diamagnetic rod levitates above the diametric magnets. The length of the rod (l) is chosen to allow stable trapping condition e.g., approximately 0.15 L<l<0.9 L where L is the length of the diametric magnet.

Further, as described in Gunawan, this system also yields a one-dimensional camelback potential along the longitudinal (z) axis stemming from the magnetic field distribution. See FIG. 1. It has been found herein that this weak confinement allows a graphite rod (in one exemplary embodiment a mechanical pencil lead) trapped in this system to oscillate. See the double sided arrow in FIG. 1 which indicates the path of oscillation of the diamagnetic rod over the magnets 102a and 102b. An actuator (described below) can be used to tilt the trap to initialize the oscillation of the diamagnetic rod. See the double sided arrow in FIG. 1 which indicates that the trap can be briefly tilted to initiate the oscillations.

This oscillation can be recorded with a motion detection system. According to an exemplary embodiment, the motion detection system includes a video camera 106 that is positioned facing a top of the PDL trap so as to permit capturing video images of the diamagnetic rod. The motion data can be sent to a computer 108. The computer will analyze the data, extract the damping time constant (due to the presence of an ambient gas), and calculate the viscosity and/or pressure of the ambient gas. An exemplary apparatus that may be implemented as computer 108 is provided in FIG. 6, described below.

One of the advantages of the present PDL trap gas analysis system is its low-cost production and maintenance. It is also compact and requires a relatively small amount of gas for measurement. This is particularly important when the gas is rare or expensive. Furthermore, this system can be miniaturized which might be valuable for certain industry applications.

The magnetic field distribution of the present PDL trap can be described as the field due to magnetic parallel dipole line. The trap has a weak camelback confinement potential (see, for example, FIG. 1) along the z-axis that allows the diamagnetic rod to oscillate. A top-down view of the PDL trap is shown in FIG. 2a. As shown in FIG. 2a, the diamagnetic rod (in this case a graphite rod) will oscillate to the left and to the right along the z-axis. As highlighted above, these oscillations can be captured using video motion analysis. See FIG. 2b. According to an exemplary embodiment, a digital video camera is used for the video motion analysis. The pixels in a digital camera collect photons which are converted into an electrical charge that represents intensity. During the motion analysis, the intensity of the image pixels can be measured from each video frame. See FIG. 2b wherein the pixel intensity is plotted along the z-axis. The position of the rod can be determined by choosing a certain intensity value that marks the edge of the rod called "edge threshold." The plot in FIG. 2b shows the positioning of the graphite rod as it appears in FIG. 2a. By capturing video of the trapped rod, one can obtain the (damped) oscillation curve of the rod and extract its parameters such as the oscillation period (T) and the damping time constant (τ). See FIG. 2c, wherein t is time, l is the length of the rod, and $z_R$ is the rod position or displacement.

The oscillation damping of the rod is due to the viscous drag (friction) of the (ambient) gas surrounding the rod. In a simple approximation of a short cylindrical rod with diameter comparable to its length, the gas viscosity μ can be calculated from the damping time constant (τ) as:

$$\mu \sim \frac{2\rho\pi rl}{C_D \tau} \quad (1)$$

wherein ρ, r, and l are the mass density, radius, and length of the rod respectively, and $C_D$ is the drag coefficient that depends on the geometry of the rod such as the length (l) and radius (r). For example when l/r>4, $C_D$ is approximately 0.81 (see, for example, Fluid Dynamic Drag, Hoerner, Hoerner Fluid Dynamics, Chapter 3, pg. 12 (3-12), 1965). For a fixed setup (e.g., the present PDL trap with a rod of known/fixed dimensions), these various factors can be lumped together as a viscosity calibration factor $k_V$:

$$\mu = k_V/\tau \quad (2)$$

The factor $k_V$ is an experimental or calibration constant independent of gas. It can be measured using gas of a known viscosity, and this step becomes the calibration step. For instance, the present PDL trap with a rod of known dimensions can be used along with an ambient gas of known viscosity. The oscillations of the rod can be measured using (e.g., video) motion analysis, and the damping time constant τ can be derived—as described above. Since both the gas viscosity μ and the damping time constant τ are known, then the factor $k_V$ in Equation 2 can be calculated.

The present system can also be utilized as a pressure gauge, i.e., a system to measure pressure at a low pressure p regime (p<$10^{-4}$ bar), e.g., for a vacuum chamber. At a high pressure regime, where the gas mean free path is much shorter than the feature size of the system, e.g., p>$10^{-4}$ bar, the gas viscosity is independent of pressure. However the "viscosity" drops at low pressure regimes and it's approximately proportional to the gas pressure. Strictly speaking at this low pressure regime, the "viscosity" being measured is no longer a characteristic of the gas—but rather is due to the geometrical characteristics of the vacuum chamber. This is because the gas mean free path is much longer than the feature size of the measurement system, e.g., the PDL trap. A system based on friction drag of a magnetically levitated rotating ball (called spinning rotor gauge) has been demonstrated to measure pressure. This system is accurate and serves as an absolute pressure measurement tool that can be used to calibrate other types of pressure gauges. See, for example, Boffito et al., "Spinning rotor gauge in the range from $10^{-4}$ Pa to atmosphere," J. Vac. Sci. Technol. A 15(4), pgs. 2391-2394, July/August 1997, the contents of which are incorporated by reference as if fully set forth herein. A similar principle can be used to perform pressure measurement using the present PDL trap system. In this system the rate of changes of rotor angular velocity is proportional to the pressure p and the mean velocity of the gas $v_g$ at pressure p impinging on the rotor surface, i.e., $(d\omega/dt)/\omega \sim -pv_g$.

The present PDL trap system can be used for pressure measurement at low pressure regime (e.g., p<$10^{-4}$ bar) by the same measurement of the rod oscillation damping time constant τ. The damping time constant τ is related to the pressure as: $\tau \sim 1/pv_g$. Since $v_g$ depends on pressure, the pressure can be simplified as a function of damping time constant τ as:

$$p = k_P/\tau \quad (3)$$

where $k_P$ is an experimental constant or pressure calibration factor for the system. It can be measured using a known gas pressure p (e.g., the pressure of a gas measured using another separate pressure gauge), and this step becomes the calibration step. For instance, the present PDL trap with a rod of known dimensions can be used along with an ambient gas at a known pressure. The oscillations of the rod can be measured using (e.g., video) motion analysis, and the damping time constant τ can be derived—as described above. Since both the pressure p and the damping time constant τ are known, then the factor $k_P$ in Equation 3 can be calculated. It is notable that the pressure versus τ can also be characterized across a wide range of pressures to anticipate non-linear behavior, e.g., at a high pressure regime (p>$10^{-4}$ bar) where the damping time constant tends to be constant due to constant gas viscosity versus pressure (i.e., near a high pressure regime (e.g., p>$10^{-4}$ bar) the damping time constant could start to be non-linear with respect to pressure and ultimately becomes constant at higher pressure due to constant viscosity—however pressure measurements can still be performed, except that the damping time constant vs. pressure needs to be calibrated/plotted in this non-linear regime). Further, it is notable that the damping time constant τ actually also depends on the diameter d of the levitated rod. See, for example, FIGS. 3a-b. Specifically, FIG. 3a is a diagram illustrating underdamped oscillation (i.e., where the amplitude gradually decays to zero) of rods of diameter d of 0.3 millimeters (mm) and 0.9 mm. As shown in FIG. 3a, the damping time constant τ (measured in seconds(s)) is greater (damping is weaker) with the larger diameter rod. Similarly, FIG. 3b which plots rod diameter d (measured in mm) as a function of the damping time constant τ (measured in s) shows that τ increases (damping becomes weaker) with a larger rod diameter. This aspect is useful for tuning the dynamic range of the measurements based on the sensitivity of the system. For instance, when the viscosity of the gas being measured is large, a rod having a larger diameter can be used to increase the sensitivity of the measurement or to ensure that the measurement can be performed in a reasonably short amount of time.

Namely, the greater the viscosity of the gas, the more friction the gas will impart on the oscillating rod. Thus, by increasing the diameter of the rod, the effect of the damping (due to the gas) can be decreased/weakened in order to permit the above-described viscosity measurements to be made. To look at it another way, if a (relatively) small diameter rod was use to measure the viscosity of a (relatively) higher viscosity gas, then the damping effect (of the gas) might not permit the transient oscillation of the rod needed to extract the viscosity. To give a simple example to illustrate this point, silane ($SiH_4$) and ammonia ($NH_4$) are common chemical vapor deposition (CVD) and atomic layer deposition (ALD) precursors. Silane has a greater viscosity (e.g., $1.070 \times 10^{-4}$ poise) than ammonia (e.g., $9.193 \times 10^{-5}$ poise). Thus, in a system employing silane as the ambient gas one might choose to use a rod of a greater diameter (e.g., d=0.9 mm) than when ammonia is the ambient gas (e.g., d=0.3 mm).

Another consideration, however, is the length of time needed to make the measurement. For instance, referring to FIG. 2c, the oscillation period T and the damping time constant τ are extracted from the rod oscillation curve that occurs over a time t. Depending on the diameter of the rod, the time t over which transient oscillation of the rod occurs varies. Compare, for example, the examples shown in FIG. 3a with rods of diameter d=0.3 mm and d=0.9 mm which exhibit transient oscillation over a period of about 15 seconds (s) and about 27 s, respectively. Thus, for a gas of a given viscosity, the rod diameter can be varied to adjust the measurement time. According to an exemplary embodiment, the rod used in the present system has a diameter of from about 0.3 mm to about 1.3 mm, and ranges therebetween.

FIG. 4 is a diagram of one exemplary configuration of the present PDL trap system. In the example shown in FIG. 4, the PDL trap system is encased within an enclosure. This will enable an ambient gas to be captured for measurement. Namely, the enclosure is fitted with an inlet door, through which the gas can be introduced into the enclosure (see gas inlet and inlet door). The present PDL trap (see PDL trap/diamagnetic magnet pair and graphite rod) is located within the enclosure situated on a tiltable platform.

The tiltable platform permits, via an actuator (in this case a shape memory alloy), one end of the PDL trap to be momentarily lifted and then returned to a horizontal orientation which serves to initialize the oscillation of the graphite rod levitating above the magnets. Namely, as shown in FIG. 4, the tiltable platform is attached to an inner surface of the enclosure via a pivoting link. The actuator is attached both to the top of the enclosure and to an end of the platform opposite the pivoting link. According to an exemplary embodiment, the actuator is a shape memory alloy that is configured to contract by a constant amount when a current is applied to it—pulling the end of the tiltable platform toward the top of the enclosure, thereby raising the end of the tiltable platform by that (constant) amount. When the current is removed, the actuator returns to its relaxed state, and the tiltable platform (and PDL trap) are returned to a horizontal orientation. Shape memory alloy wires which may be used as an actuator are commercially available, for example, from Dynalloy, Inc., Irvine, Calif. The use of a tiltable platform and shape memory alloy actuator are merely an example meant to illustrate the present techniques. In practice, any means for jolting the platform/PDL trap to initiate oscillation of the rod may be employed such as using a solenoid actuator, a small electric motor, etc. According to an exemplary embodiment, the platform/PDL trap starts at a horizontal orientation (i.e., at an angle θ of 0 degrees (°) relative to the bottom of the enclosure—see FIG. 4). When the actuator is activated, the platform/PDL trap is raised at an angle θ of from about 10° to about 30°, and ranges therebetween relative to the bottom of the enclosure, for a duration of from about 1 second to about 3 seconds, and ranges therebetween, after which the platform/PDL trap is returned to the horizontal orientation.

Stopper guards are located on opposite ends of the PDL trap (i.e., on opposite ends of the path of oscillation of the rod along the z-axis—see, e.g., FIG. 2*a*). The stopper guards serve to physically prevent the levitating graphite rod from travelling past the ends of the magnets during oscillation. The stopper guards may be made from any suitable non-metallic/non-magnetic material, such as plastic, rubber, etc.

In this exemplary embodiment, the oscillating motion of the rod is captured using a digital video camera. As shown in FIG. 4, the digital video camera is located in a top of the enclosure and is positioned facing the top of the PDL trap and the rod (i.e., the video camera has a top down view of the PDL trap and oscillating rod—in the same manner as shown in FIG. 2*a*). As described above, the video camera will capture video images of the rod oscillating over the magnets.

As shown in FIG. 4, the video camera, the actuator, and the enclosure inlet door are all controlled by a microcomputer. An exemplary apparatus that may be implemented as the microcomputer is provided in FIG. 6, described below. Specifically, the microcomputer will coordinate opening/closing the inlet door to capture a gas sample within the enclosure, activate the actuator (e.g., provide momentary current to shape memory alloy) to tilt the platform and thereby initiate oscillation of the rod, and start the video camera to record the oscillations. In turn, the video camera will relay the digital video images of the oscillating rod to the microcomputer where the data is analyzed (as described in detail above) to extract the oscillation and its parameters (such as the oscillation period T and the damping time constant τ) which are used to calculate the viscosity and/or pressure of the gas. The results of the analysis can be revealed on a display or readout, such as a standard computer monitor.

An exemplary methodology 500 for analyzing a gas using the present PDL trap system is now described by way of reference to FIG. 5. The process begins in step 502 by capturing a sample of the gas. According to an exemplary embodiment, the PDL trap system is configured as shown in FIG. 4 to include an inlet door through which the gas is introduced to the enclosure. As provided above, the inlet door can be controlled by a microcomputer which can open the inlet door (e.g., via a standard motor gear drive or other similar actuator) to receive the gas sample, and then close the inlet door to ensure that no air agitation occurs during the viscosity measurement. By way of example only, the microcomputer may control opening the inlet for a certain duration (e.g., from about 1 second to about 10 seconds, and ranges therebetween), during which time an ambient gas passively enters the enclosure. Alternatively, a gas sample might be injected into the enclosure through the inlet opening.

In step 504, oscillation of the rod over the magnets is initiated. As provided above, oscillation of the rod can be initiated simply by jolting the PDL trap. According to an exemplary embodiment, the PDL trap system is configured as shown in FIG. 4 to include an actuator (such as a shape memory alloy, solenoid actuator, or electric motor attached to the platform and to the top of the enclosure) that is configured to tilt the PDL trap thereby initiating oscillation of the rod. For instance, using a shape memory alloy actuator as an example, a current can be applied to the shape memory alloy to cause it to constrict (by a constant amount)—pulling the end of the tiltable platform toward the top of the enclosure, thereby raising the end of the tiltable platform. A solenoid actuator or electric motor would operate in the same manner to tilt the platform. For instance, with a linear solenoid actuator an applied current moves a plunger a fixed distance. When the current is removed, the plunger returns to its original position. This movement of the plunger can be used to tilt the platform. Similarly, an electric motor with a drive gear can be used to raise/lower the platform when a current is supplied to the motor. Preferably, stopper guards are implemented (as described above) in order to prevent the rod from travelling past the ends of the magnets.

In step 506, once jolted, one must wait (approximately five oscillation periods) for transient oscillation of the rod to occur. During this initial transient period, the rod could develop some additional random motion or oscillation mode (e.g., torsional mode along its vertical axis) that decays more quickly.

In step 508, video of the rod oscillation is recorded. According to an exemplary embodiment, the PDL trap system is configured as shown in FIG. 4 including a digital video camera and a microcomputer that coordinates the video camera with the inlet door and the actuator. Namely, following activation of the actuator to initiate motion of the rod, the microcomputer then begins the video camera recording the oscillating motion of the rod. The video is then relayed from the video camera to the microcomputer where it is analyzed—see step 510.

In step 510, the video is analyzed. Video motion analysis can be carried out, as described above, to extract the oscillation of the rod and its parameters, such as the oscillation period T and the damping time constant τ. According to an exemplary embodiment, the PDL trap system is configured as shown in FIG. 4 and the video motion analysis is carried out by the microcomputer.

As provided above, an initial calibration of the system may be performed, i.e., prior to measuring the viscosity of an unknown gas. To calibrate the system, steps 502-510 can be carried out with a rod of known/fixed dimensions, and a gas of known viscosity and/or pressure. Based on the calibration via steps 502-510, the damping time constant τ can be measured and, along with the known gas viscosity, used to determine the factor $k_V$ (see Equation 2)—which as described above is an experimental viscosity constant independent of the gas being measured. Similarly, the damping time constant τ (measured in steps 502-510) along with a gas at a known pressure (i.e., measured separately with another pressure gauge) can be used to determine the factor $k_P$ (see Equation 3)—which as described above is an experimental pressure constant independent of the gas being measured.

If the process is in this calibration phase (Yes), then as per step 512 methodology 500 ends (since the viscosity of the gas for calibration purposes is already known), and the process can be repeated with an unknown gas sample. In subsequent iterations, the same/fixed rod dimensions for which the system has been calibrated are used. Alternatively, if it is determined in step 512 that this is not the calibration phase of the process (No) (e.g., the system has already been calibrated in an earlier run, and is now being used to measure an unknown sample), then the process continues at step 514 to calculate the (unknown) viscosity and/or pressure of the gas.

Namely, in step 514 at high pressure regimes (e.g., $p>10^{-4}$ bar) the (unknown) viscosity of the gas can be calculated using Equations 1 and 2 above, and at low pressure regimes (e.g., $p<10^{-4}$ bar) the (unknown) pressure of the gas can be calculated using Equation 3 above. It may be desirable to take multiple readings to increase the accuracy of the measurement. That decision is made in step 516, i.e., whether or not to repeat the measurement process. If it is determined in step 516 (Yes) to perform multiple readings, then the process can be repeated beginning at step 504 where the PDL trap is jolted (as described above) to initiate oscillation of the rod and, once transient oscillation is achieve, another reading is performed using video motion analysis, etc. When multiple readings are made, the average of the readings can be taken as the measured gas viscosity. By way of example only, the average of from 3-10 iterations of the process may be employed. If/when it is determined in step 516 (No) that no more iterations are needed, then the process ends.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
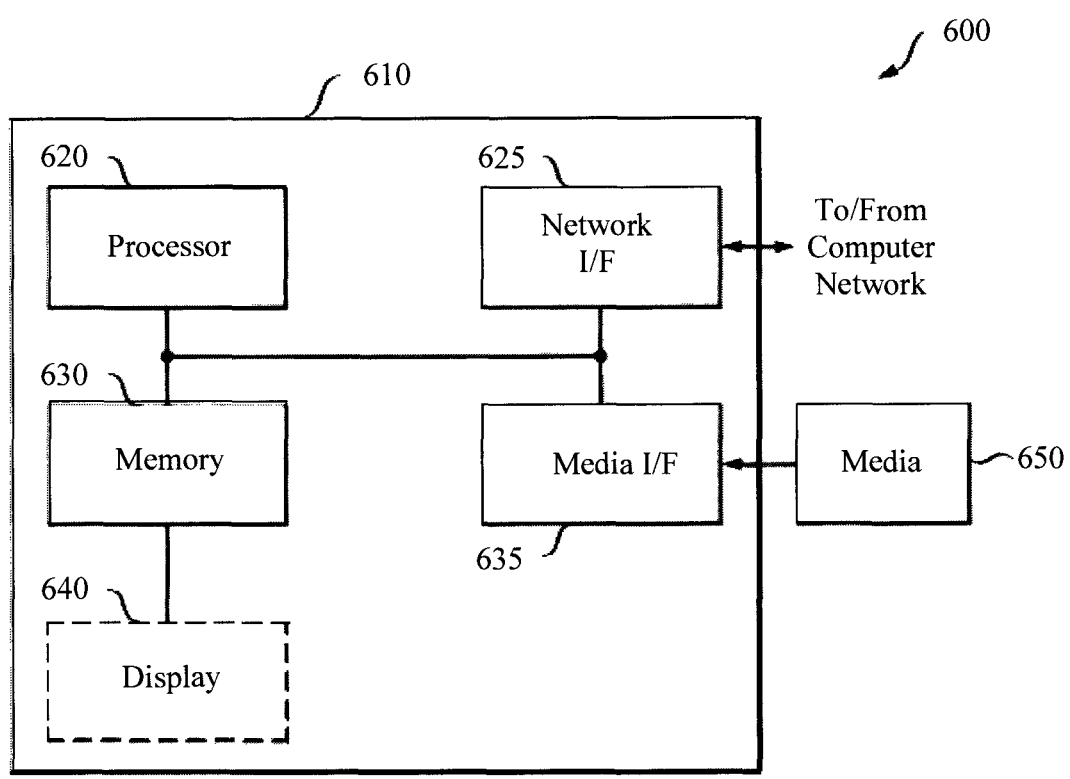
FIG. 6 is a diagram of an exemplary apparatus for implementing one or more of the methodologies presented herein according to an embodiment of the present invention.

Turning now to FIG. 6, a block diagram is shown of an apparatus 600 for implementing one or more of the methodologies presented herein. By way of example only, apparatus 600 can be implemented as the computer 108/microcomputer in FIG. 1 and FIG. 4, respectively.

Apparatus 600 includes a computer system 610 and removable media 650. Computer system 610 includes a processor device 620, a network interface 625, a memory 630, a media interface 635 and an optional display 640. Network interface 625 allows computer system 610 to connect to a network, while media interface 635 allows computer system 610 to interact with media, such as a hard drive or removable media 650.

Processor device 620 can be configured to implement the methods, steps, and functions disclosed herein. The memory 630 could be distributed or local and the processor device 620 could be distributed or singular. The memory 630 could be implemented as an electrical, magnetic or optical memory, or any combination of these or other types of storage devices. Moreover, the term "memory" should be construed broadly enough to encompass any information able to be read from, or written to, an address in the addressable space accessed by processor device 620. With this definition, information on a network, accessible through network interface 625, is still within memory 630 because the processor device 620 can retrieve the information from the network. It should be noted that each distributed processor that makes up processor device 620 generally contains its own addressable memory space. It should also be noted that some or all of computer system 610 can be incorporated into an application-specific or general-use integrated circuit.

Optional display 640 is any type of display suitable for interacting with a human user of apparatus 600. Generally, display 640 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A gas analysis system, comprising:
    a parallel dipole line (PDL) trap comprising: a pair of diametric cylindrical magnets, and a diamagnetic rod levitating above the pair of diametric cylindrical magnets;
    a motion detector for capturing motion of the diamagnetic rod; and
    a tiltable platform, wherein the PDL trap is present on the tiltable platform.

2. The gas analysis system of claim 1, wherein the diamagnetic rod comprises a graphite rod.

3. The gas analysis system of claim 1, further comprising:
    stopper guards on opposite ends of the PDL trap to prevent the diamagnetic rod from traveling past the ends of the PDL trap.

4. The gas analysis system of claim 1, wherein the PDL trap is encased within an enclosure.

5. The gas analysis system of claim 4, wherein the enclosure comprises an inlet door to permit a gas to be introduced into the enclosure.

6. The gas analysis system of claim 1, further comprising:
    an actuator attached to an end of the tiltable platform, wherein the actuator is configured to raise the end of the tiltable platform.

7. The gas analysis system of claim 6, wherein the actuator comprises a shape memory alloy.

8. The gas analysis system of claim 1, wherein the motion detector comprises a digital video camera positioned facing a top of the PDL trap so as to permit capturing video images of the diamagnetic rod.

9. The gas analysis system of claim 8, further comprising a computer for receiving and analyzing video images from the video camera.

10. A method for analyzing a gas, the method comprising the steps of:
    providing a gas analysis system comprising i) a PDL trap having a pair of diametric cylindrical magnets, and a diamagnetic rod levitating above the pair of diametric cylindrical magnets; and ii) a motion detector for capturing motion of the diamagnetic rod, wherein the PDL trap is encased within an enclosure;
    introducing the gas to the enclosure;
    initiating oscillation of the diamagnetic rod over the pair of diametric cylindrical magnets;
    recording motion of the diamagnetic rod using the motion detector;
    determining a damping time constant $\tau$ from the recorded motion of the diamagnetic rod; and
    calculating a viscosity $\mu$ of the gas using the damping time constant $\tau$.

11. The method of claim 10, wherein the enclosure comprises an inlet door, the method further comprising the steps of:
    opening the inlet door;
    introducing the gas to the enclosure through the inlet door; and
    closing the inlet door.

12. The method of claim 10, wherein the gas analysis system further comprises stopper guards on opposite ends of the PDL trap to prevent the diamagnetic rod from traveling past the ends of the PDL trap once oscillation of the diamagnetic rod has been initiated.

13. The method of claim 10, wherein $\mu = k_v/\tau$, and wherein $k_v$ is a viscosity measurement calibration factor for the gas analysis system and is independent of the gas being analyzed.

14. The method of claim 10, further comprising the steps of:
repeating the initiating, recording, determining, and calculating steps to obtain multiple viscosity measurements for the gas; and
determining an average of the multiple viscosity measurements.

15. The method of claim 10, wherein the motion detector comprises a digital video camera positioned facing a top of the PDL trap, and wherein the step of recording motion of the diamagnetic rod comprises the step of:
recording a digital video image of the oscillation of the diamagnetic rod using the digital video camera.

16. The method of claim 15, further comprising the step of:
determining the damping time constant $\tau$ from the digital video image of the oscillation of the diamagnetic rod.

17. The method of claim 10, wherein gas analysis system further comprises a tiltable platform and an actuator attached to an end of the tiltable platform, wherein the PDL trap is present on the tiltable platform, and wherein the oscillation of the diamagnetic rod is initiated by using the actuator to raise the end of the tiltable platform.

18. The method of claim 17, wherein the actuator is attached to both the end of the tiltable platform and a top of the enclosure.

19. The method of claim 18, wherein the actuator comprises a shape memory alloy, the method further comprising the step of:
applying a current to the shape memory alloy to cause the shape memory alloy to constrict and pull the end of the tiltable platform toward the top of the enclosure thereby raising the end of the tiltable platform.

* * * * *